US010654200B2

(12) United States Patent
Bacchereti et al.

(10) Patent No.: US 10,654,200 B2
(45) Date of Patent: May 19, 2020

(54) APPARATUS AND METHOD FOR PRODUCING A BIOCOMPATIBLE THREE-DIMENSIONAL OBJECT

(71) Applicant: S.M. Scienzia Machinale S.R.L., Cascina (IT)

(72) Inventors: Marco Bacchereti, Cascina (IT); Luca Bosio, Pisa (IT); Giorgio Soldani, Massa (IT)

(73) Assignee: S.M. Scienzia Machinale S.R.L., Cascina (IT)

(*) Notice: Subject to any disclaimer, the term of this patent is extended or adjusted under 35 U.S.C. 154(b) by 913 days.

(21) Appl. No.: 14/852,326

(22) Filed: Sep. 11, 2015

(65) Prior Publication Data

US 2016/0001469 A1 Jan. 7, 2016

Related U.S. Application Data

(63) Continuation-in-part of application No. 14/838,205, filed on Aug. 27, 2015, and a continuation of (Continued)

(30) Foreign Application Priority Data

Mar. 7, 2013 (IT) .............................. PI2013A0015

(51) Int. Cl.
*B29C 41/08* (2006.01)
*G05B 19/4099* (2006.01)
(Continued)

(52) U.S. Cl.
CPC ............ *B29C 41/08* (2013.01); *A61F 2/2415* (2013.01); *B29C 41/34* (2013.01); *B29C 41/365* (2013.01);
(Continued)

(58) Field of Classification Search
None
See application file for complete search history.

(56) References Cited

U.S. PATENT DOCUMENTS 4,538,364 A * 9/1985 Jensen .................. B65D 88/72
34/170
6,581,437 B2 * 6/2003 Chrystall ............. A43D 999/00
73/7

(Continued)

FOREIGN PATENT DOCUMENTS

JP 2006509658 3/2006
JP 2012-236125 6/2012
(Continued)

OTHER PUBLICATIONS

PCT International Written Opinion of the International Searching Authority dated Sep. 8, 2016 in corresponding PCT Application No. PCT/IB2016/001377, inventor, Marco Bacchereti, et al.

*Primary Examiner* — Matthew J Daniels
*Assistant Examiner* — Mohammad M Ameen
(74) *Attorney, Agent, or Firm* — Steptoe & Johnson LLP

(57) ABSTRACT

An apparatus for making a biocompatible three-dimensional object including at least one delivery unit arranged to deliver at least one biocompatible fluid substance towards a 3D mold having a matrix surface to obtain a coating layer of a predetermined thickness configured for coating the matrix surface. The three-dimensional object may be a heart valve. Furthermore, a handling unit is provided arranged to provide a relative movement according to at least 3 degrees of freedom between the 3D mold and each delivery unit. The 3D mold is arranged to be coated by the delivered biocompatible fluid substance, in order to obtain a three-dimensional object having an object surface copying the matrix surface of the support body.

14 Claims, 12 Drawing Sheets

Related U.S. Application Data application No. PCT/IB2014/059291, filed on Feb. 27, 2014.

(51) Int. Cl.

| | | |
|---|---|---|
| *B29C 41/34* | (2006.01) | |
| *B29C 41/36* | (2006.01) | |
| *A61F 2/24* | (2006.01) | |
| *B29L 31/00* | (2006.01) | |
| *B33Y 10/00* | (2015.01) | |
| *B33Y 30/00* | (2015.01) | |
| *B33Y 80/00* | (2015.01) | |

(52) U.S. Cl.
CPC .... *G05B 19/4099* (2013.01); *A61F 2240/001* (2013.01); *B29K 2995/0056* (2013.01); *B29L 2031/7532* (2013.01); *B33Y 10/00* (2014.12); *B33Y 30/00* (2014.12); *B33Y 80/00* (2014.12)

(56) References Cited

U.S. PATENT DOCUMENTS

| | | | |
|---|---|---|---|
| 2004/0123435 A1* | 7/2004 | Soldani | B01D 67/0004 28/100 |
| 2007/0076197 A1* | 4/2007 | Koga | G01N 21/94 356/237.3 |
| 2013/0015596 A1* | 1/2013 | Mozeika | B25J 9/0084 264/40.1 |
| 2013/0052291 A1* | 2/2013 | Morikawa | B29C 64/153 425/135 |

FOREIGN PATENT DOCUMENTS

| | | |
|---|---|---|
| WO | 200245933 A2 | 6/2002 |
| WO | 2010136983 | 12/2010 |
| WO | 2013019416 A1 | 2/2013 |
| WO | 2014136021 A1 | 9/2014 |

\* cited by examiner

APPARATUS AND METHOD FOR PRODUCING A BIOCOMPATIBLE THREE-DIMENSIONAL OBJECT

CROSS-REFERENCE TO RELATED APPLICATIONS

This application is a continuation-in-part of U.S. application Ser. No. 14/838,205, filed Aug. 27, 2015, which is a continuation of International Application No. PCT/IB2014/059291, filed Feb. 27, 2014, which claims priority to Italian Patent Application No. PI2013A000015, filed Mar. 7, 2013, each of which is incorporated by reference in their entirety.

FIELD

The present disclosure relates to an apparatus for making a biocompatible three-dimensional object with complex shape, i.e. made of two or more surfaces presenting different radius of curvature. In particular, the present disclosure relates to the production of tissues as well as biocompatible and blood-compatible membranes for making vascular prostheses, concave or convex heart patches, ellipsoidal cardiac chambers, patches for calcaneal ulcers, or other components of anatomical parts. The present disclosure relates also to a method for making such three-dimensional objects.

BACKGROUND

As well known, many techniques and apparatus exist for making tissues and biocompatible artificial membranes. In particular, the main known techniques provide the production of the above described artificial tissues by extrusion, or by spraying fluid substances. More in detail, the spraying techniques provide the deposit of a polymeric solution of synthetic origin by overlapping the polymeric solution in diluted form and a non-solvent, for example water, to each other. To this purpose a sprayer is used which sprays both substances in an alternated way, or, alternatively, two sprayers are used that deliver the two substances at the same time. The substances are deposited on a support body which has the same geometry of the desired tissue products or artificial membranes.

An example of an apparatus for making such membranes by spraying is disclosed in WO200405477. The apparatus uses a plurality of sprayers, each of them drawing from a respective reserve a component of the biological mixture. A cylindrical support element is then arranged on which the fluid substances supplied by the sprayers are deposited, in order to make a coating that forms the desired membranes. The cylindrical support element can kinematically rotate about a fixed rotation axis, whereas the sprayers are moved by a carriage that makes a translational movement along an axis that is substantially parallel to the rotation axis of the cylindrical support element. This way, the fluid substances supplied can deposit on the whole surface of the support element.

However, this solution, as it can be understood, is applicable only in case the membranes to make have a relatively simple and regular shape with surfaces presenting a wide radius of curvature and not too suddenly variable. Such membranes should also have substantially axisymmetric shape, in order to keep a constant spraying flow during the rotation of the support element.

A similar apparatus is disclosed in WO2010136983. Even in this case, the apparatus is used for making a biocompatible structure that allows regenerating biological tissues with simple shape. Notwithstanding the above, the apparatus as above described for making tissues or biocompatible artificial membranes cannot provide anatomical. prostheses with complex shape, such as concave or convex heart patches, ellipsoidal cardiac chambers, patches for calcaneal ulcers, or portions of organs.

U.S. Pat. No. 5,376,117 describes a breast prosthesis for subcutaneous implants. The prosthesis consists of an outer shell comprising a non-porous layer of biocompatible polymeric material and a porous outer layer that coat wraps the non-porous layer. The outer layer is made by electrostatic deposit of biocompatible polymeric fibers on the inner layer. Once obtained the three-dimensional structure, the prosthesis is overturned and arranged on a spindle that is rotated about its own axis, in order to make the convex side of the prosthesis.

A breast prosthesis obtained by a process similar to that described in U.S. Pat. No. 5,376,117 is disclosed also in WO2010/059834. However, both processes, as described in U.S. Pat. No. 5,376,117 and WO2010/059834, are not suitable for the production of tissues and biocompatible artificial membranes with complex shape and with small tolerances, since they cannot ensure an accurate definition of the modelled forms.

SUMMARY

Existing limitations associated with the foregoing, as well as other limitations, can be overcome by an apparatus for and method for producing a biocompatible object. Briefly, and in general terms, the present disclosure is directed to various embodiments of an apparatus for and method for producing a biocompatible object.

In general terms, the present disclosure provides an apparatus that allows the production of a biocompatible three-dimensional object with complex shape, i.e. not necessarily equipped with significant symmetries and, in particular with surfaces having different radius of curvature. The present disclosure may also provide an apparatus that allows for the production of such three-dimensional object with high dimensional precision, in order to copy accurately a pre-designed model.

Further, the present disclosure may provide an apparatus that allows programming the whole production work so that it can be carried out in an automatic way.

Briefly, and in general terms, the present disclosure is directed to an apparatus for making a biocompatible three-dimensional object. The apparatus includes at least one delivery unit arranged to deliver at least one biocompatible fluid substance towards a support body, also called core, that has a matrix surface, to obtain a coating layer of a predetermined thickness configured for coating the matrix surface. The biocompatible fluid substance may include a plurality of particles. The apparatus also includes a handling unit for determining a relative movement according to at least 3 degrees of freedom between the support body and the delivery unit. This is so that the support body may be coated with the delivered biocompatible fluid substance to obtain a three-dimensional object having an object surface copying the matrix surface of the support body. Further, the apparatus includes a suction and blowing unit is also provided configured to provide a suction and blowing current arranged to remove from the support body any surplus particles of the biocompatible fluid substance supplied by the or each delivery unit. In this example, it is possible to deposit a uniform predetermined thickness of coating layer on the matrix surface. The solution provided by the present disclosure, and in particular the possibility of actuating relatively the support body and the delivery unit according to at least 3 degrees of freedom during the coating steps of the matrix surface, makes it possible to control with high precision the deposit of the biocompatible fluid substance on the matrix surface. It is also possible to adjust, in a correspondingly precise way and as it is needed, the thickness of the layers of deposited fluid substance. This is possible since the handling unit is capable to expose the matrix surfaces of the support body to a jet of biocompatible fluid substance supplied by the delivery unit, positioning this matrix surface substantially orthogonally to the jet.

After the deposit of the fluid substances, the coating is removed from the support body giving rise to the sought three-dimensional object.

In certain embodiments, the handling unit is arranged to provide a relative movement according to 4 degrees of freedom, advantageously, according to 5 degrees of freedom, preferably according to 6 degrees of freedom. In one embodiment, the handling unit includes an anthropomorphic robot having a chain of pivot joints that has an end connected to a fixed base and the other end connected to a support base to which the support body, and/or the delivery unit, can be mounted in a removable way. Such chain of pivot joints is adapted to actuate the support body, and/or the delivery unit, according to at least 6 degrees of freedom, supplying higher design precision in generating the sought three-dimensional object.

Alternatively, the handling unit may include a plurality of actuators, each of which has one end engaged with a fixed base and another end engaged with a support base to which the support body, and/or the delivery unit, can be mounted in a removable way.

In certain embodiments, the actuators may be pneumatic actuators, hydraulic actuators, electric actuators, or a combination thereof.

In one embodiment, the suction and blowing unit may be replaced with a suction device, or the suction and blowing unit may include a suction device and a blowing device. The suction device may be a fixed suction device. Alternatively, the suction device can be a movable suction device associated with auxiliary moving means arranged to move the suction device, in order to follow spatially the position of the support body during its handling by the handling unit. This way, any surplus particles of the biocompatible fluid substance can be removed regardless of the position of the support body.

In a further exemplary embodiment, the suction device may include a suction hood integral to the support base and configured to surround laterally the support body, in order to maximize the suction of any surplus particles of the biocompatible fluid substance. A suction tube may also be included which is arranged to connect pneumatically the suction hood with a suction system. This way, it is not necessary the implementation of the auxiliary moving means, since the hood is in an optimal position for suction of any surplus particles of the biocompatible fluid substance, whichever is the position of the support body. In one embodiment, the hood may have a toroidal, cylindrical, or tubular shape.

In one embodiment, the suction device may include a storage reservoir of any surplus particles or a filter on which such particles can deposit. Furthermore, the suction or blowing current from the suction and blowing unit can be generated by a fan or a compressor located upstream of the suction tube.

In one example, the apparatus may include a first delivery unit arranged to deliver a first jet of a first biocompatible fluid substance towards the support body. The first biocompatible fluid substance being a biomaterial of synthetic origin. The apparatus of this embodiment also may include a second delivery unit arranged to deliver a second jet of a second biocompatible fluid substance towards the support body. The second biocompatible fluid substance being a non-solvent, for example, water. The second delivery unit is arranged to direct the second delivery jet towards the support body, in order to overlap the second delivery jet to the first delivery jet. This may induce a quick deposit of the synthetic biomaterial supplied onto the support body by the first delivery unit, obtaining a filamentous three-dimensional structure.

In yet another embodiment, the apparatus also includes a counter-mold. The counter-mold may be adapted, once ended the delivery of the biocompatible fluid substances, to press, in particular to heat, the coating layer that is deposited on the support body. This is to obtain a better finishing of the shape of the three-dimensional object, in addition to improved mechanical features.

In another embodiment, the apparatus also includes third delivery unit arranged to deliver a third biocompatible fluid substance, in particular diluted in solution, both of synthetic and biological origin. In certain embodiments with two or three delivery units, with respective delivery of jets of biocompatible fluid substances, there may be a program means configured for combining the alternation of such delivery. This way, the step of coating can be completely automated, and does not require, in normal conditions, manual monitoring.

Also, in one embodiment, a control means is also provided for monitoring the thickness of the formed coating layer, in order to test that the coating layer has thickness corresponding to that of the designed coating layer. In particular, the designed coating layer can be provided to apparatus by a control CAD.

The current disclosure is also directed to a method for making a biocompatible three-dimensional object. The method includes the step of delivery of at least one biocompatible fluid substance towards a support body, also called core, which has a matrix surface. Also, the method includes obtaining a coating layer of predetermined thickness configured for coating the matrix surface. The delivery occurring using at least one delivery unit. The method also includes handling the support body and/or the delivery unit with a handling unit, in order to provide a relative movement according to at least 3 degrees of freedom between the support body and the delivery unit. This is so that the support body is coated with the delivered biocompatible fluid substance to obtain a three-dimensional object having an object surface copying the matrix surface. There may be multiple delivery units and the at least 3 degrees of freedom may be between the support body and each of the delivery units. The method also includes removing from the support body any surplus particles of the biocompatible fluid substance dispensed with a suction and blowing unit. The removing being carried out through a suction or a blowing step, in order to make uniform the predetermined thickness of the coating layer. The suction and blowing unit may be replaced with a suction device or a blowing device.

Further, the current disclosure discloses a method to produce a biocompatible three-dimensional heart valve. The method includes the step of determining a size and geometry of the heart valve and producing, using a computer processor, a virtual three-dimensional model of the heart valve based on the predetermined size and geometry. The method also includes creating a three-dimensional mold and a counter mold of the virtual three-dimensional model of the heart valve and spraying a layer of a biocompatible polymeric resin on the surface of the three-dimensional mold. A stent may also be disposed on the mold and covered with a layer of biocompatible polymeric resin. The method further includes pressing the counter mold on the biocompatible polymeric resin layer covered surface of the three-dimensional mold and allowing the biocompatible polymeric resin layer to cure and dry in situ. The method also includes extracting the dry biocompatible polymeric resin layer covered three-dimensional mold from the counter mold and removing the dry biocompatible polymeric resin layer from the three-dimensional mold.

In one embodiment, the size of the heart valve is determined by different scanning techniques, for example, CT, FL, DR and MRI. In another embodiment, the geometrical design of the heart valve is one of narrow orifice, symmetrical leaflets or asymmetrical leaflets. In yet another embodiment, the three-dimensional mold and the counter mold of the virtual three-dimensional model of the heart valve are created using a rapid prototyping process, for example, vacuum casting.

Other features and advantages will become apparent from the following detailed description, taken in conjunction with the accompanying drawings, which illustrate by way of example, the features of the various embodiments.

BRIEF DESCRIPTION OF THE DRAWINGS

The present disclosure will be now shown with the following description of some exemplary embodiments thereof, exemplifying but not limitative, with reference to the attached drawings in which.

DETAILED DESCRIPTION

Each of the features and teachings disclosed herein can be utilized separately or in conjunction with other features and teachings to provide an apparatus for and method for producing a biocompatible object. Representative examples utilizing many of these additional features and teachings, both separately and in combination are described in further detail with reference to the attached figures. This detailed description is merely intended to teach a person of skill in the art further details for practicing aspects of the present teachings and is not intended to limit the scope of the claims. Therefore, combinations of features disclosed above in the detailed description may not be necessary to practice the teachings in the broadest sense, and are instead taught merely to describe particularly representative examples of the present teachings.

In the description below, for purposes of explanation only, specific nomenclature is set forth to provide a thorough understanding of the present disclosure. However, it will be apparent to one skilled in the art that each of these specific details are not required to practice the teachings of the present disclosure.

Moreover, the various features of the representative examples may be combined in ways that are not specifically and explicitly enumerated in order to provide additional useful embodiments of the present teachings. It is also expressly noted that all value ranges or indications of groups of entities disclose every possible intermediate value or intermediate entity for the purpose of original disclosure. It is also expressly noted that the dimensions and the shapes of the components shown in the figures are designed to help to understand how the present teachings are practiced, but not intended to limit the dimensions and the shapes shown in the examples. In this document, measurements, values, shapes, angles, and geometric references (such as perpendicularity and parallelism), when associated with words like "about" or other similar terms such as "approximately" or "substantially," should be construed to allow for measurement errors or others errors due to production and/or manufacture process, and may vary by up to ten percent.

Figure 1:
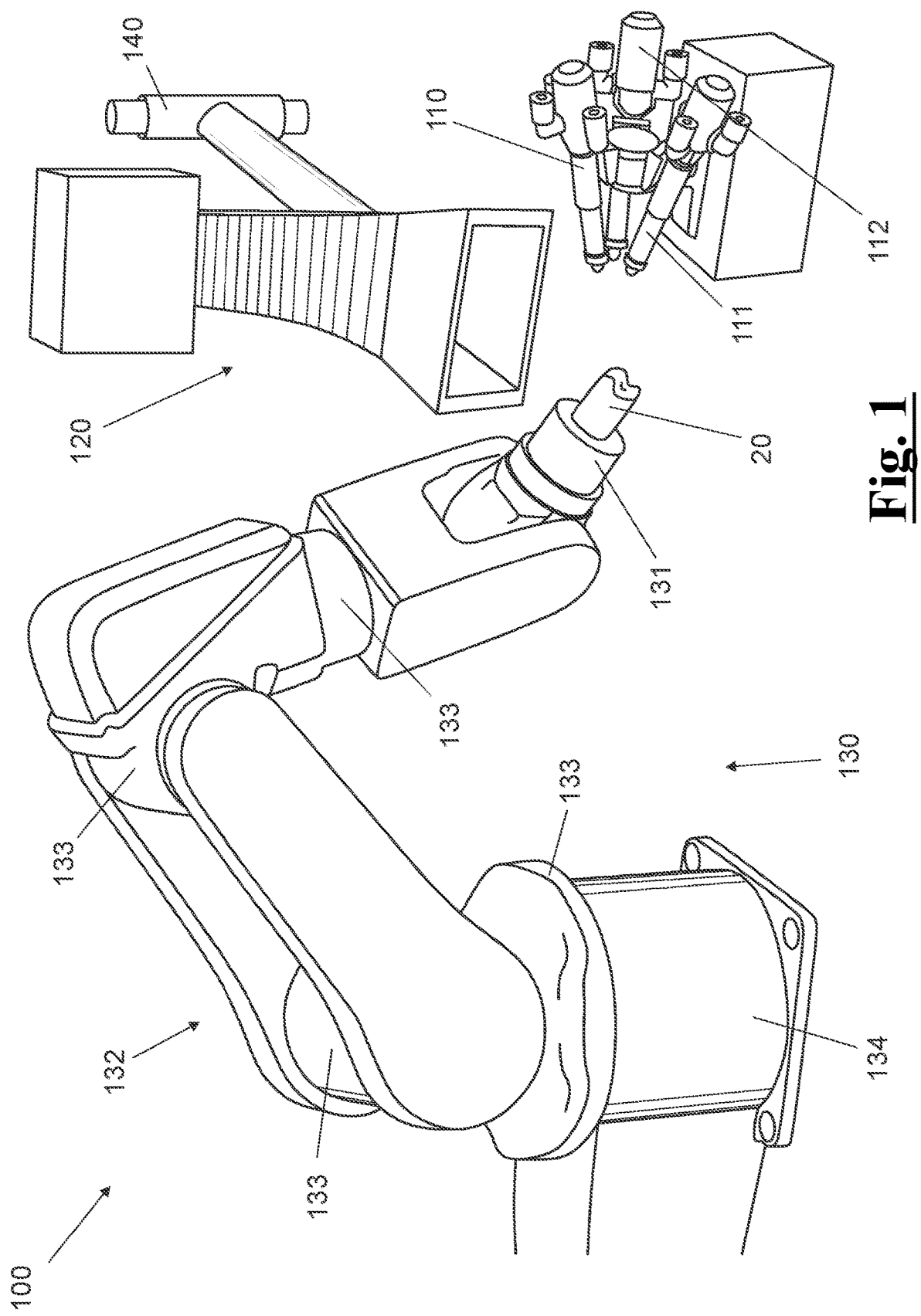
FIG. 1 shows an exemplary embodiment of an apparatus including an anthropomorphic robot arranged to handle the support body.

With reference to FIG. 1, an exemplary embodiment of an apparatus 100 for making a biocompatible three-dimensional object 30 provides an anthropomorphic robot 132 having a kinematical chain of pivot joints 133. Such chain of joints 133 is constrained at an end to a fixed base 134, and at another end to a support base 131 on which support body 20 engages in a removable way. The chain of pivot joints 133 of FIG. 1 allows handling the support body according to six degrees of freedom, allowing an optimum precision when generating the sought three-dimensional object 30.

In FIG. 1, three delivery units 110,111,112 are shown that are arranged to deliver three different biocompatible fluid substances. Fewer or more delivery units can be arranged to deliver biocompatible fluid substances. In particular, first delivery unit 110 is adapted to deliver a jet of a biomaterial of synthetic origin towards the support body 20. The second delivery unit 111 is, instead, arranged to deliver a jet of non-solvent, for example water, overlapping to the jet generated by first delivery unit 110, in order to induce a quick deposit of the biopolymeric material supplied onto support body 20 by first delivery unit 110, allowing to obtain a filamentous three-dimensional structure. The third delivery unit, finally, is adapted to deliver a third biocompatible fluid substance diluted in solution, in particular another biomaterial of synthetic or biological origin.

Each delivery unit 110,111,112 also has a hydraulic circuit (not shown in the figure, for example, a cylinder-piston mechanism) consisting of ducts, with possible valves and pumps, which connect the or each delivery unit to reservoirs containing the biocompatible fluid substances.

In this exemplary embodiment, a suction and/or blowing unit 120 is further provided, adapted to generate a suction and/or blowing current. This way, the suction and/or blowing unit 120 makes it possible to level the thickness of the coating layer 35 and to remove from support body 20 any surplus particles of the biocompatible fluid substances supplied by the or each delivery unit 110, 111, 112. The device 120 is also spatially moved by auxiliary moving means 140, in such a way that this device 120 can follow spatially the position of support body 20 during its handling steps by handling unit 130. In some embodiments, the base 134 of the handling unit 130 can be automated or free such that it is controlled by a user. Moreover, the structure of the handling unit 130 is not limited to the structure shown in the figures.

Figure 2:
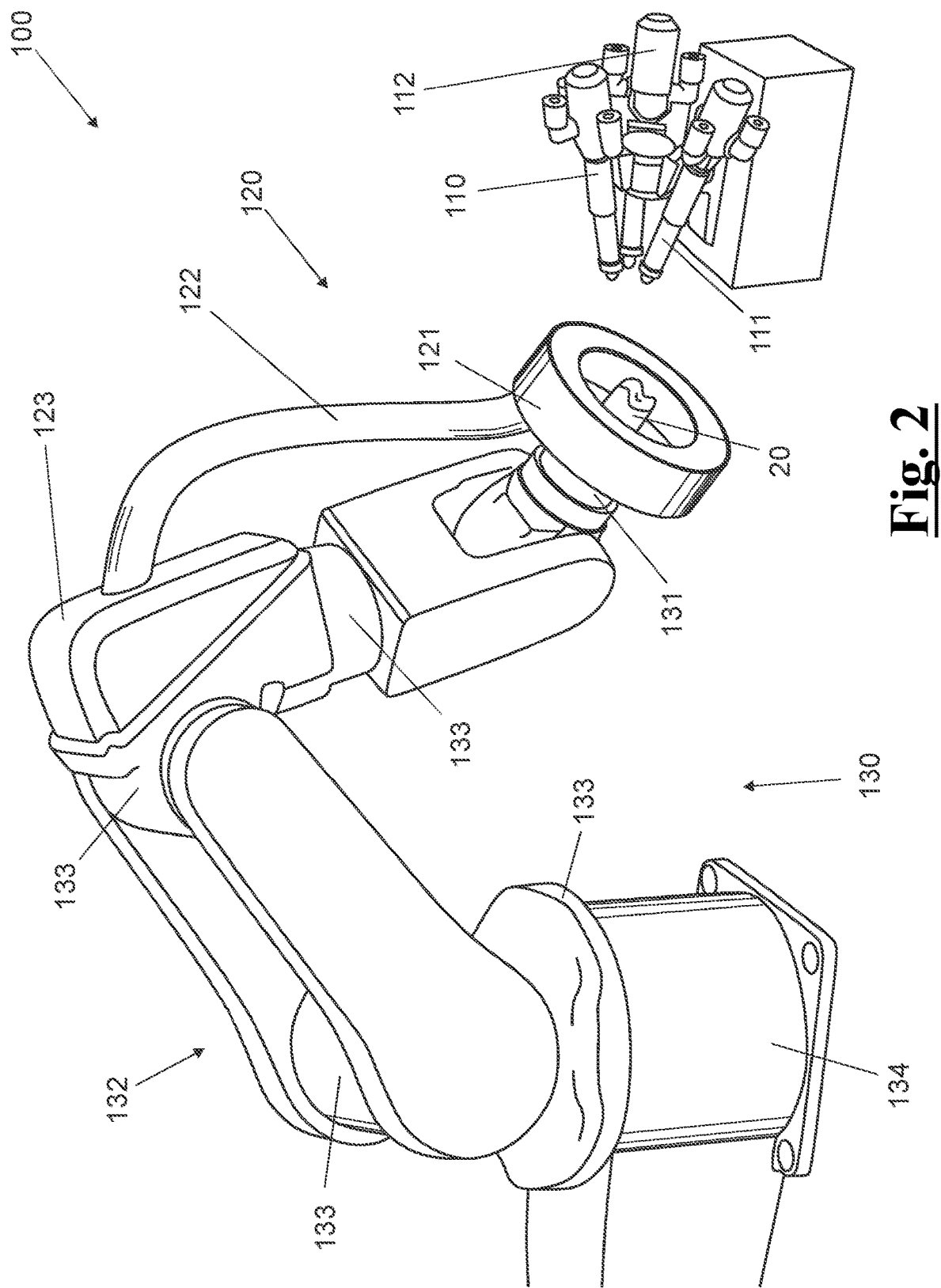
FIG. 2 shows an exemplary embodiment of an apparatus, which differs from that of FIG. 1 for the presence of a toroidal hood arranged to surround the support body.

In FIG. 2 a second exemplary embodiment is shown, which differs from an exemplary embodiment of FIG. 1 as from the type of the device 120. In this exemplary embodiment, device 120 includes a toroidal suction hood 121, which is integral to support base 131 and is configured to surround laterally support body 20. Toroidal hood 121 is then joined to a suction tube 122 arranged in turn to connect pneumatically the suction hood 121 with a suction system 123 that has a compressor to generate a suction flow and with a storage reservoir containing any surplus particles of the dispensed fluid substance.

Alternatively, in an exemplary embodiment not shown in the figures, device 120 is a blowing device including a compressor adapted to generate a blowing current for removing any surplus particles of the delivered fluid substance. This way, it is not necessary that the apparatus includes auxiliary handling unit 140, like the exemplary embodiment of FIG. 1, since the toroidal hood 121 surrounds laterally the support body 20, whichever is the position reached by handling unit 130. However, in some embodiments, any surplus particles of the delivered fluid substance can be removed by laser or other abrading method.

Figure 3:
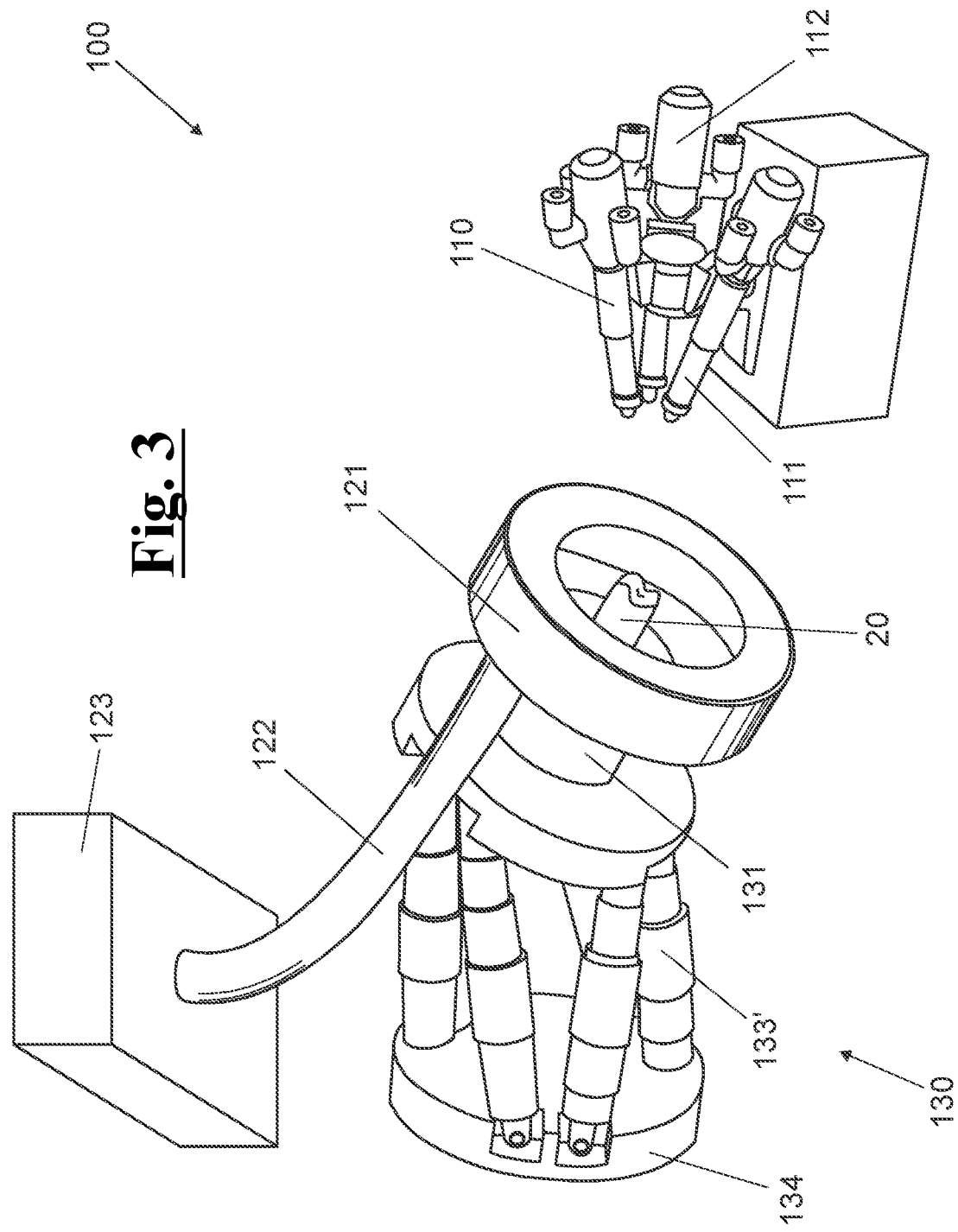
FIG. 3 shows an exemplary embodiment of the apparatus, which differs from that of FIG. 2 since the handling unit the support body does not include an anthropomorphic robot, but a plurality of linear actuators.

In FIG. 3 an exemplary embodiment is shown where handling unit 130, instead of including the anthropomorphic robot 132 of the previous figures, includes a plurality of linear actuators 133, each of which engages, at one end, to fixed base 134, and at another end, to support base 131. Support body 20 engages in a removable way with support base 131, like the previous exemplary embodiments. The handling unit can reach the same degrees of freedom of an anthropomorphic robot, even if with narrower handling range. The advantage offered by this solution is shown by a high reduction of the encumbrance.

Figures 4, 5:
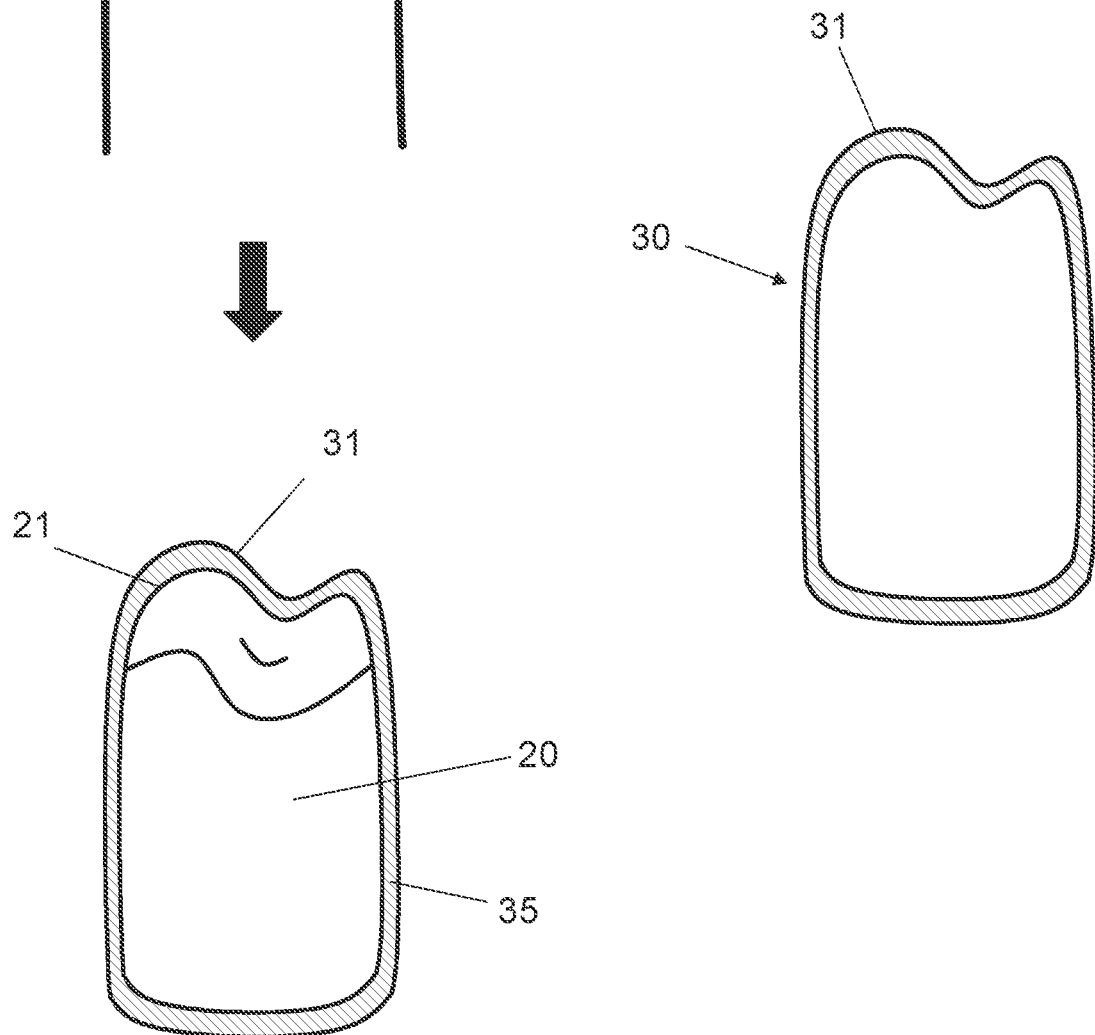
FIG. 4 shows a counter-mold that allows a hot molding of the coating layer.
FIG. 5 shows a three-dimensional object resulting from the production process.

In FIG. 4 the step is shown of pressing, in particular to hot pressing, of the coating layer 35 deposited by the or each delivery unit 110,111,112, using a counter-mold 150. The coating layer 35 is then removed from support body 20 and becomes substantially the final biocompatible three-dimensional object 30, visible in FIG. 5.

Owing to the hot pressing an optimum finishing of the shape of the three-dimensional object 30 can be achieved, in such a way that such shape is closest to the designed patch shape, for example provided by CAD or the like. Such pressing operation also gives to the three-dimensional object 30 mechanical improved features, reaching any design standards.

The apparatus 100, as described above, and shown in FIGS. 1 to 5, provides biocompatible three-dimensional objects 30 of whichever shape. In particular, biocompatible three-dimensional objects 30 can be manufactured both of simple and regular shape, such as a tetrahedron or a cone, and of irregular shape and/or with surfaces which cannot worked out in a simple way, such as a concave or convex patch or an ellipsoidal patch. Furthermore, biocompatible three-dimensional objects 30 can be provided having surfaces with different radius of curvature and/or with different angles.

Figure 6A:
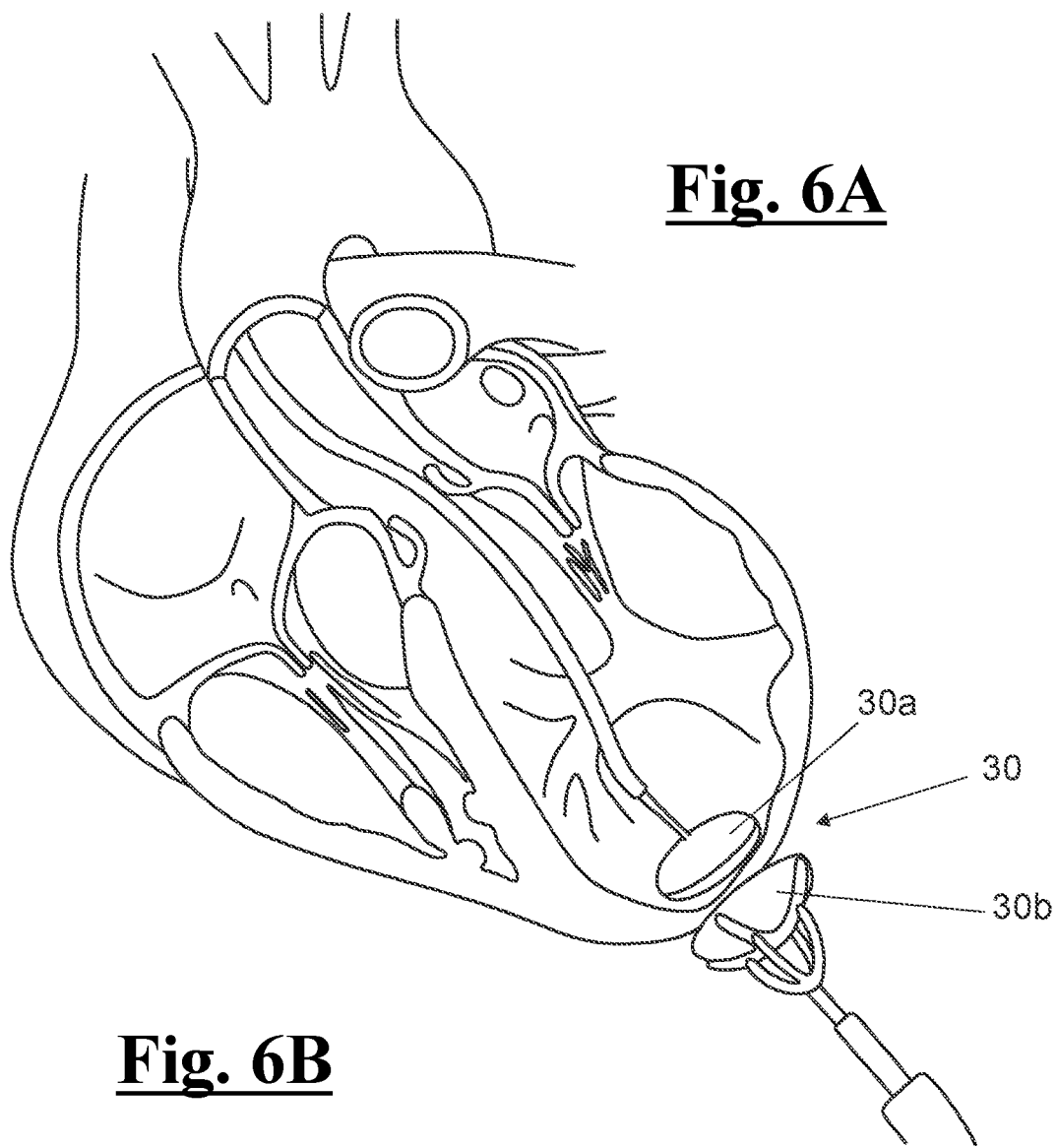
FIG. 6A shows a cardiac chamber with a heart patch applied to it.

In FIG. 6A a cardiac chamber of a human heart is shown to which a biocompatible three-dimensional object 30 is mounted, in particular a heart patch, consisting of an inner portion 30a and an external portion 30b.

Figure 6B:
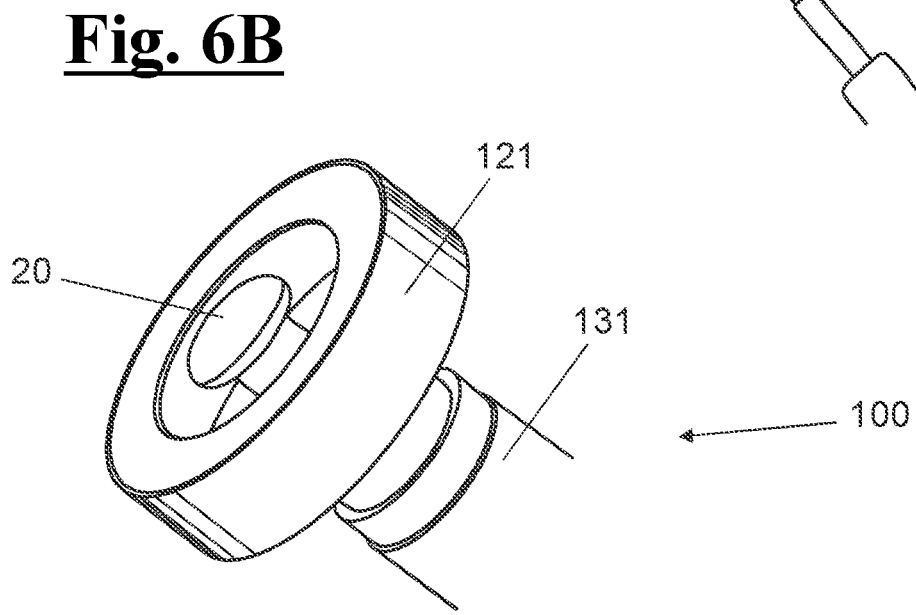
FIG. 6B shows a support from which the heart patch of FIG. 6A is generated.

In FIG. 6B part of the apparatus 100 including the support 20 is shown, from which the inner portion 30a of the heart patch of FIG. 6A is generated.

By way of example only, and not by way of limitation, a system for creating a heart valve will now be described. In one embodiment, FIG. 7 discloses a system 700 for making a synthetic, biocompatible three-dimensional (3D) heart valve 701 (shown in FIG. 13A). The system 700 includes an anthropomorphic robot 132 (e.g.; ABB IRB 120 industrial robot or the like), as described above, stationed on a workbench 712. The system also includes a 3D mold 702 mounted on a support body 20. In this example, the 3D mold 702 is for a heart valve, however, the mold maybe shaped to design for any other object. The anthropomorphic robot 132 also includes a chuck 131 to releasably hold the support body 20 and the 3D mold 702. Two spray guns 110 and 111, as described above, are also shown disposed on the workbench 712. However, a person skilled in the art can appreciate that a plurality of spray guns can be used depending on the desired heart valve structure. By way of example only, and not be way of limitation, the system may have up to 10 delivery units or spray guns. Also attached to the workbench 712 are two continuous pumps 704 and an air compressor 705. A chemical container 706 is also shown, and the chemical container 706 may store one or more biocompatible fluid substances, to be sprayed on the 3D mold 702. In certain embodiments, multiple containers may be used to store different biocompatible substances to be sprayed through one or both of the spray guns 110 and 111. The chemical container 706 is attached to one or both of the two continuous pumps 704. An electronic control unit 707 may be disposed on or near the workbench 712 and be in communication with the anthropomorphic robot 132. In one embodiment, the electronic control unit 707 may supply power and operating instructions to the anthropomorphic robot 132, pumps 704, air compressor 705, and/or spray guns 110 and 111. A suction and/or blowing unit 120 (not shown in FIG. 7) may also be provided with the system 700.

FIG. 8A discloses a close up view of the top section of the system 700 including the anthropomorphic robot 132, the 3D mold 702, two spray guns 110 and 111, and a suction and/or blowing unit 120. As mentioned above, the anthropomorphic robot 132 includes a kinematical chain of pivot joints 133. Such chain of joints 133 is constrained at an end to a fixed base 134, and at another end to a support base 131 on which support body 20 engages in a removable way. The support base 131 may be a chuck in certain embodiments.

The chain of pivot joints 133 allows handling of the support body according to six degrees of freedom, which in turn allows an optimum precision when generating the sought 3D heart valve 701.

Moreover, as shown in FIG. 8A, two delivery units 110,111 of a spraying group are arranged to deliver two different biocompatible fluid substances. In particular, first delivery unit 110 is adapted to deliver a jet of a biomaterial of synthetic origin towards the 3D mold 702 in the same manner as described above with reference to spray coating the support body 20. The second delivery unit 111 is arranged to deliver a jet of non-solvent, for example, water, overlapping to the jet generated by the first delivery unit 110 in order to induce a quick deposit of the biopolymeric material supplied onto 3D mold 702 by the first delivery unit 110. Subsequently, obtaining a filamentous 3D structure of the desired heart valve 701.

FIG. 8A also shows a suction and/or blowing unit 120 to generate suction and/or blowing current. By using the suction and/or blowing unit 120 the thickness of a coating layer on the 3D mold 702 can be levelled and surplus particles of the biocompatible fluid substances supplied by the each delivery unit 110 and 111 can be removed from support body 20. In one embodiment, the delivery units 110 and 111 are equipped with a 90 degree end axis in order to check the spraying process over a 3D valve shape. The delivery units 110 and 111 may move about an axis during the spraying process to create the 3D valve shape. FIG. 8B shows an exploded view of the 3D mold.

As described above, the suction and/or blowing unit 120 is also spatially moved by auxiliary moving means 140, in such a way that this device 120 can follow spatially the position of 3D mold 702 during its handling steps by handling unit 130 (also as described above). In some embodiments, the suction and/or blowing unit 120 can host a removable platform for maintenance aims.

Figure 9:
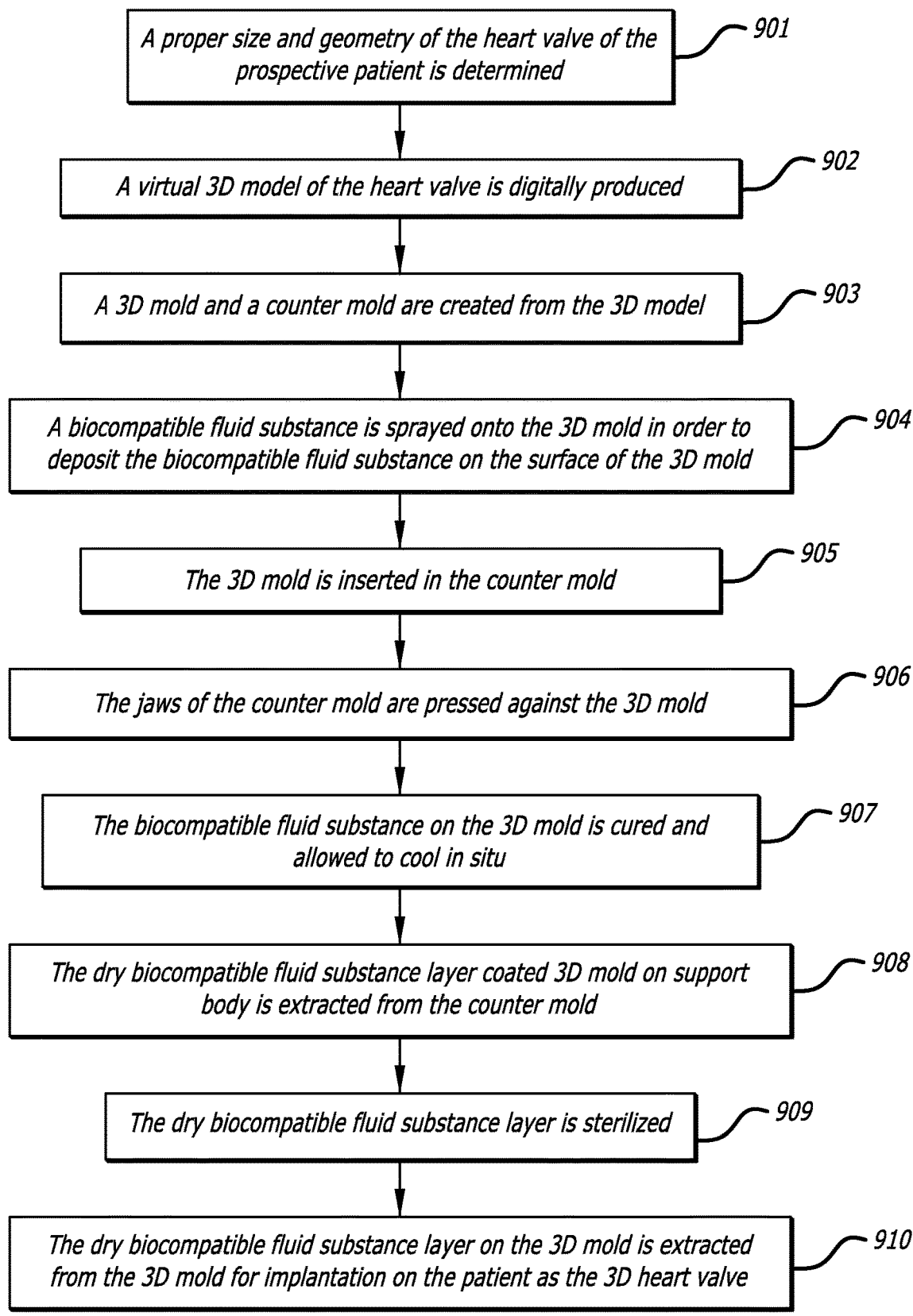
FIG. 9 shows a flow chart for one embodiment of a method for creating a 3D heart valve.

According to one embodiment, FIG. 9 discloses a method 900 to make the synthetic, biocompatible 3D heart valve 701 of this example using the anthropomorphic robot 133. In one embodiment, the anthropomorphic robot may have three to six degrees of freedom.

Figure 10A:
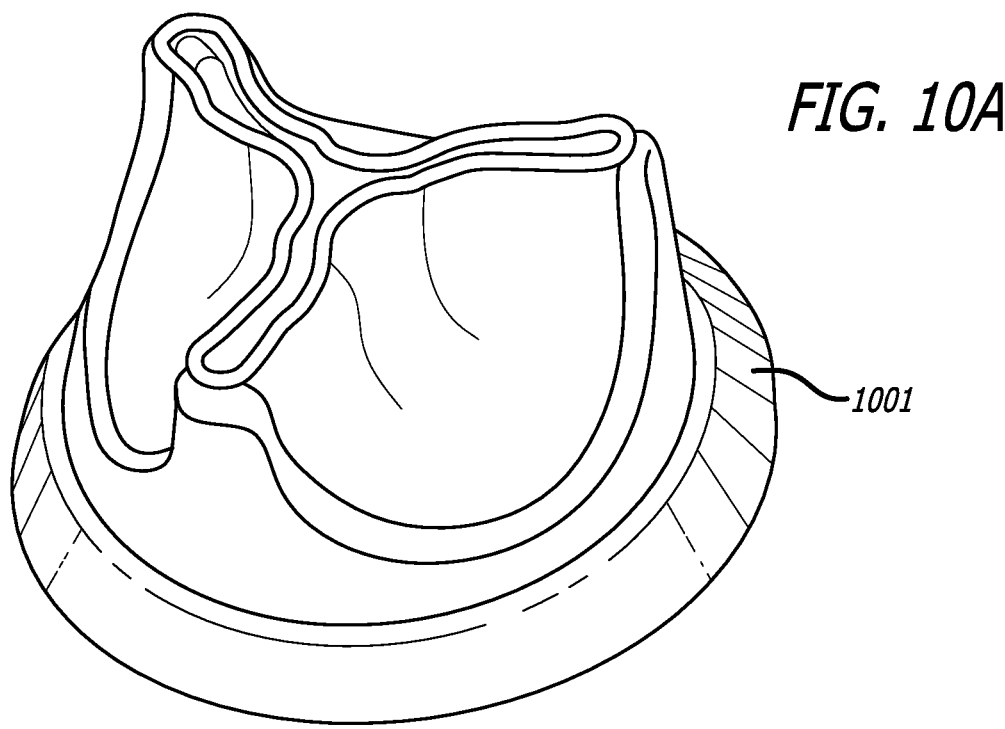
FIGS. 10A and 10B show an example of a heart valve having asymmetric leaflets.
Figure 10B:
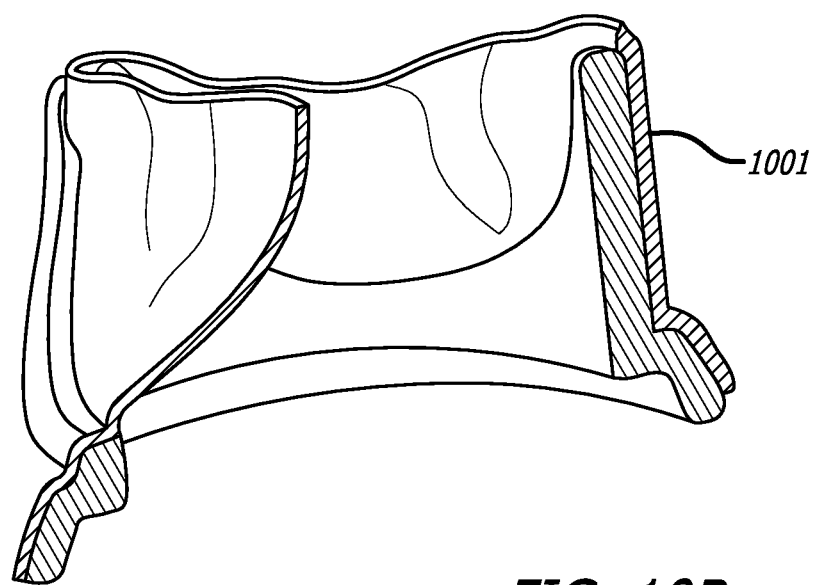
Figure 11A:
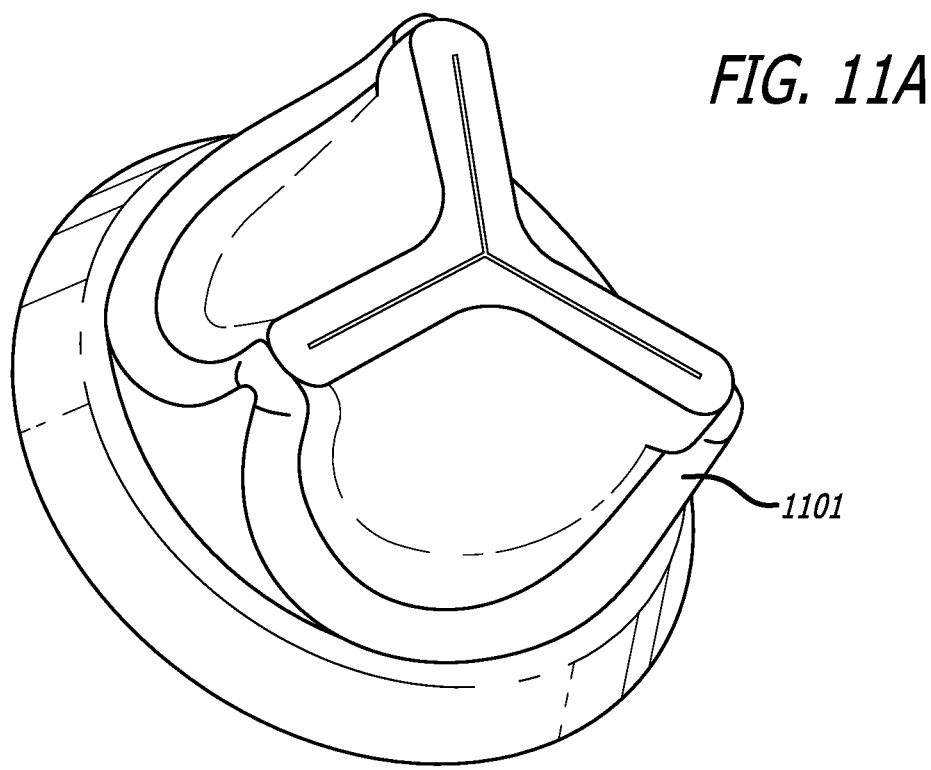
FIGS. 11A and 11B show an example of a heart valve having a narrow orifice.
Figure 11B:
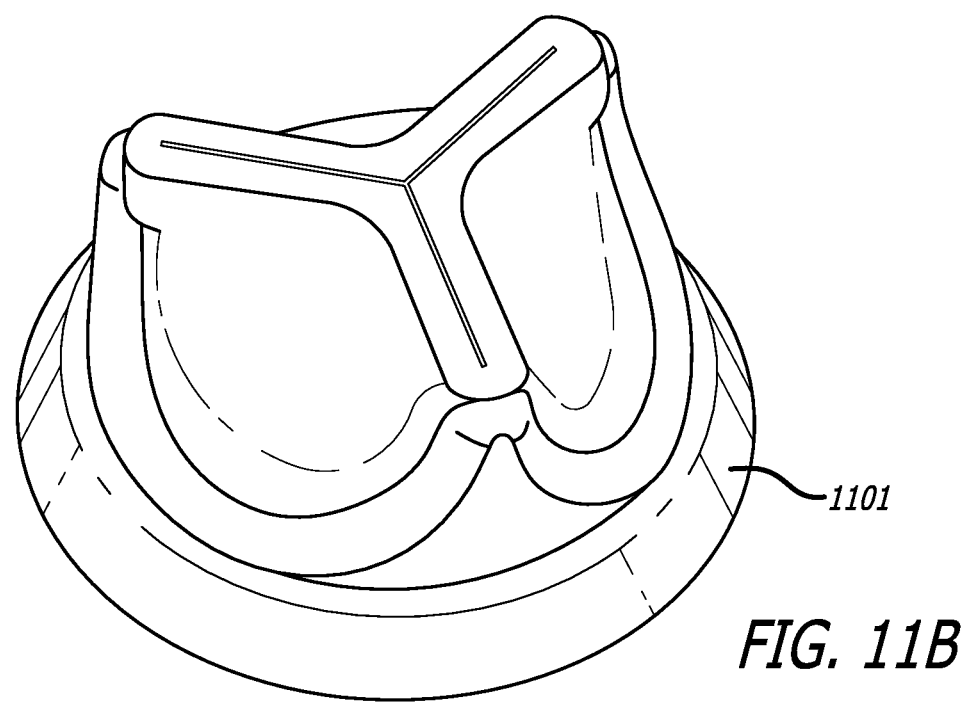
Figure 12A:
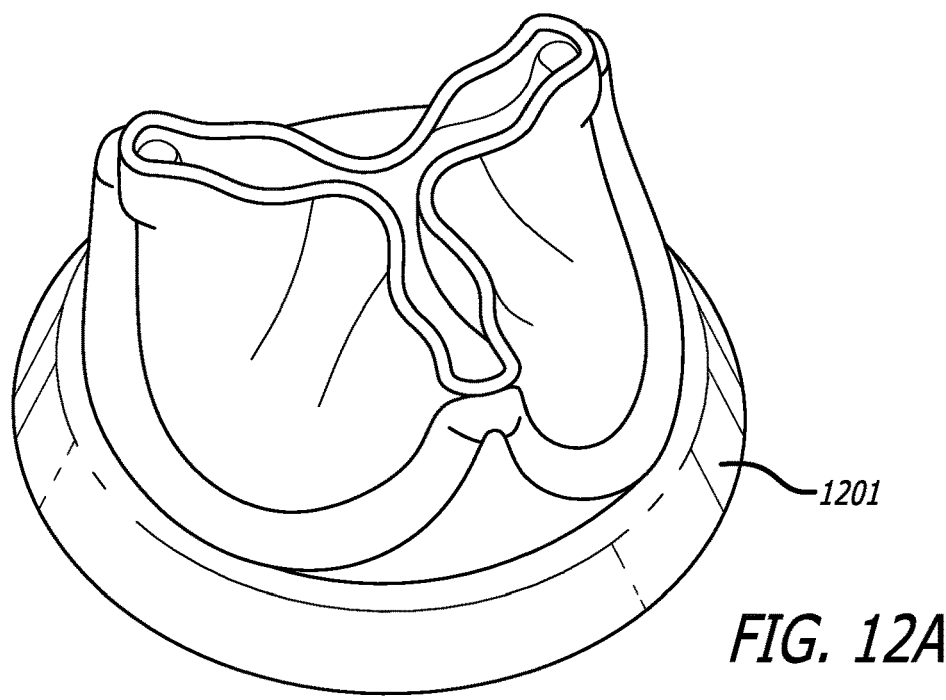
FIGS. 12A and 12B show an example of a heart valve having symmetric leaflets.
Figure 12B:
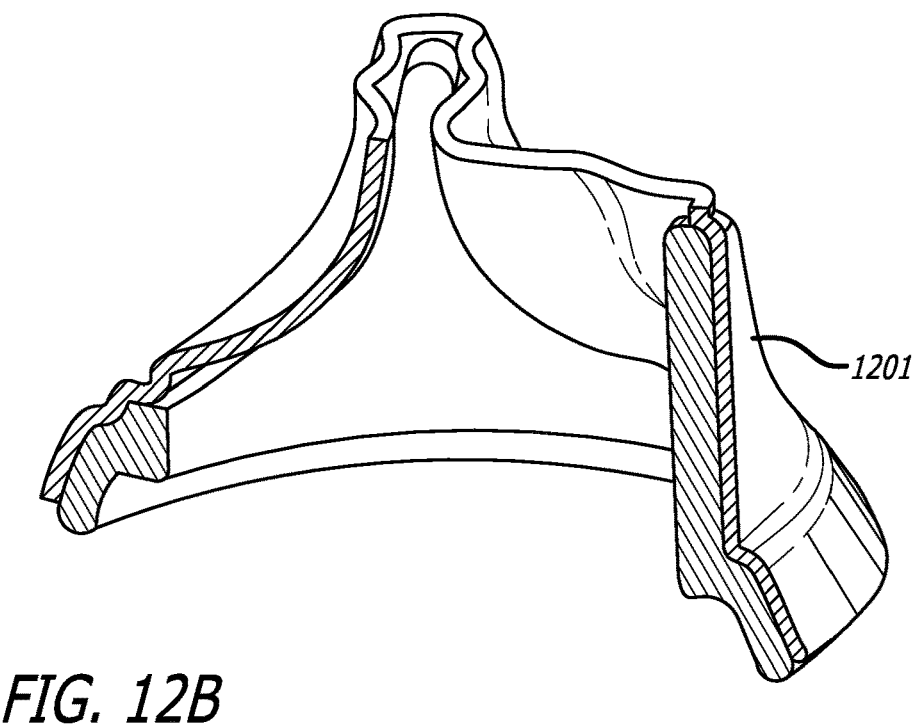

At the first step 901 of the method 900, a proper size and geometry of the heart valve 701 of the prospective patient is determined. In one embodiment, sizing the heart valve 701 is achieved by scanning (e.g.; via CT, FL, DR, MRI and the like) or visually inspecting the implantation site (i.e.; prospective patient's heart). The geometry of the heart valve is selected based on the desired characteristic of the heart valve 701 (shown in FIG. 13A). Such geometry may differ depending on the size and condition of the heart of the patient. For example, as shown in FIGS. 10A-10B, a heart valve 701 with asymmetrical leaflets geometry may be chosen. Such design geometry may offer improved valvular closure capability and may preserve opening efficiency. However, other geometrical designs (e.g. narrow orifice, symmetrical leaflets or the like) can be chosen for the heart valve 701 as well, depending on the desired characteristic. For example, as shown in FIGS. 11A-11B, a heart valve with a narrow orifice 1101 geometry may be chosen, which offers biocompatible design, simple leaflets geometry and good closure capability. On the other hand, as shown in FIGS. 12A-12B, a heart valve with a symmetrical leaflets design 1201 may be chosen, which may offer improved valve opening, since the warps in this design increases the surface of each leaflets. It should be understood that various designs may be chosen for the heart valve depending on the desired characteristics for the patient.

Once the proper size and geometry of the desired heart valve 701 is determined, at the next step 902, a virtual 3D model 708 of the heart valve 701 is digitally produced. Although a 3D model 708 of the desired heart valve may be created by hand or other machinery, it is preferred to create a virtual 3D model 708 of the heart valve. In one embodiment, the virtual 3D model 708 may be created using 3D computer-aided design (CAD) software.

At the next step 903, a 3D mold 702 and a counter mold 709 (FIG. 13B) may be created from the virtual 3D model 708. Different techniques, for example, 3D rapid prototyping process, vacuum casting, 3D printing, or the like, can be used to create the 3D mold 702 and the counter mold 709. In some embodiments, the mold and the counter mold can be made of steel to improve the quality of the 3D heart valve architecture.

In some embodiments, a stent 710 can be placed on the 3D mold 702, in order to incorporate the stent into the inner walls of the 3D heart valve 701. A stent 710 incorporated with the heart valve 701 is best shown in the exploded view of FIG. 13A. The stent 710 can be incorporated into the heart valve 701 by forming a coating around the stent 710 and the 3D mold 702 during the spraying process to form the heart valve 701. In other embodiments, the stent 710 can be incorporated into the heart valve 701 after the heart valve 701 is created. This may be done by attaching the stent 710 inside or around the exterior surface of the heart valve 701. A stent 710 maintains the cross-sectional shape of the 3D heart valve 701 and can help secure the 3D heart valve 701 within the patient, e.g., by suturing the stent and valve in position within the patient. As shown in the figures, the cross-sectional shape of the heart valve is generally circular in shape at one end, however the cross sectional shape of the heart valve may take on other shapes. Stents usually are made of metal mesh, but sometimes they can be made of fabric.

Figure 7:
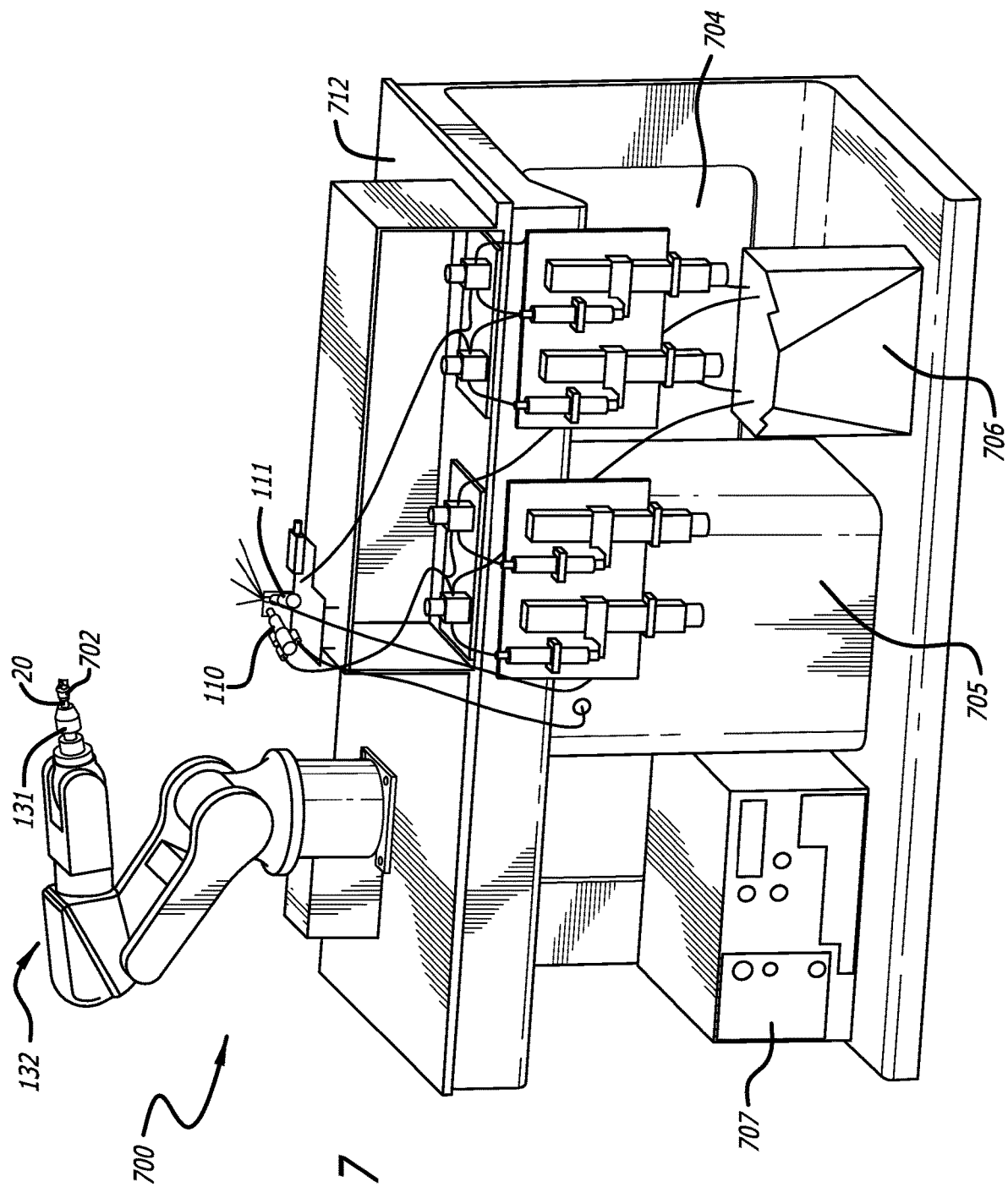
FIG. 7 shows an example of workstation for a three-dimensional spraying system including the anthropomorphic robot.
Figure 8:
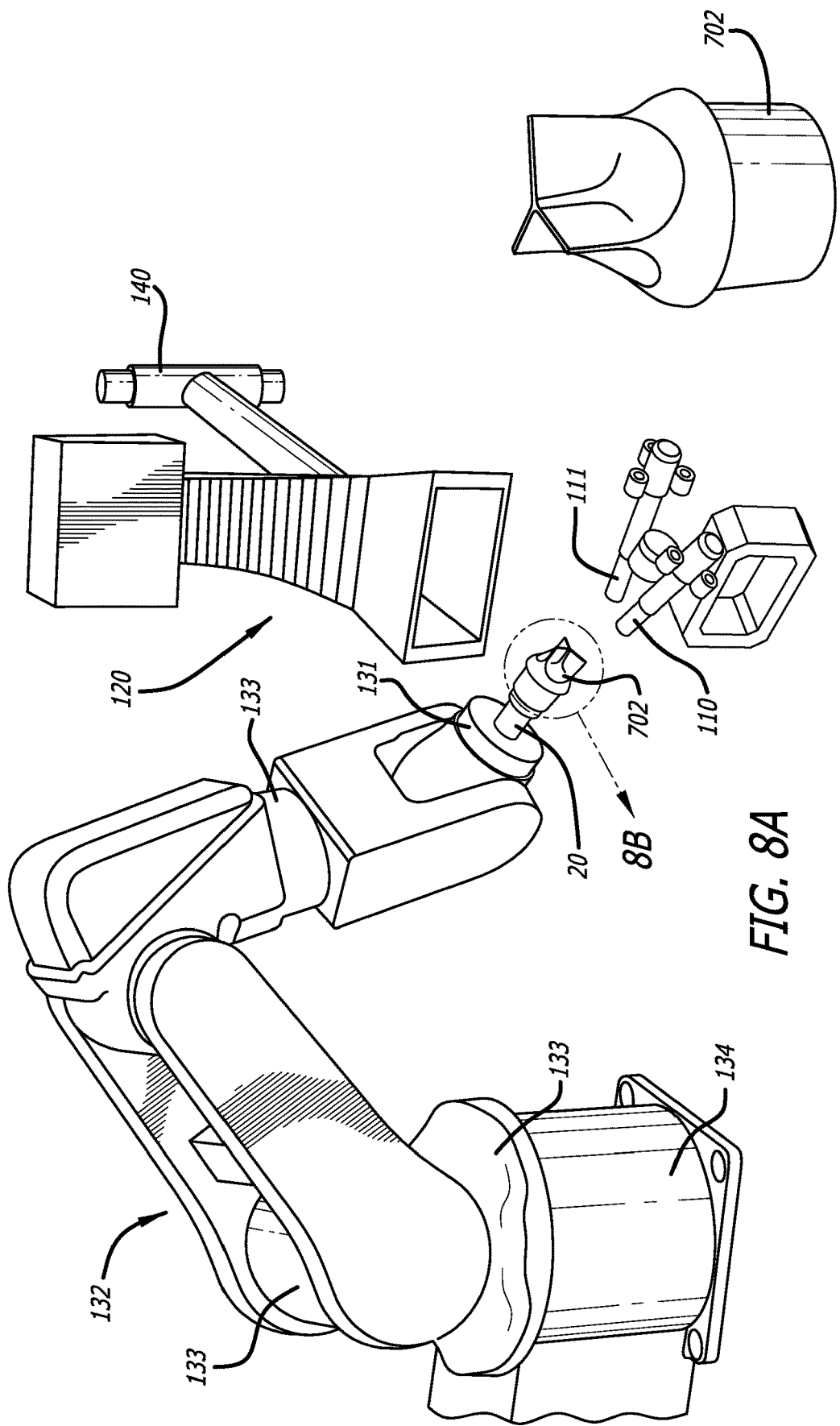
FIGS. 8A and 8B show an exemplary embodiment of an apparatus including an anthropomorphic robot arranged to handle a 3D mold of a heart valve and an exploded view of the 3D mold.

Next at step 904, a biocompatible fluid substance is sprayed onto the 3D mold 702 in order to deposit the biocompatible fluid substance on the surface of the 3D mold 702, and in certain embodiments, on the surface of a stent 710 too. The spraying of the biocompatible fluid substance onto the 3D mold 702 is shown in FIGS. 7 and 8. In this embodiment, different biocompatible fluids, for example, biocompatible polymeric resin, elastomer biomaterial, polyurethane, silicone based fluids, or the like can be used depending on the desired characteristics of the heart valve 701.

Figures 13A, 13B:
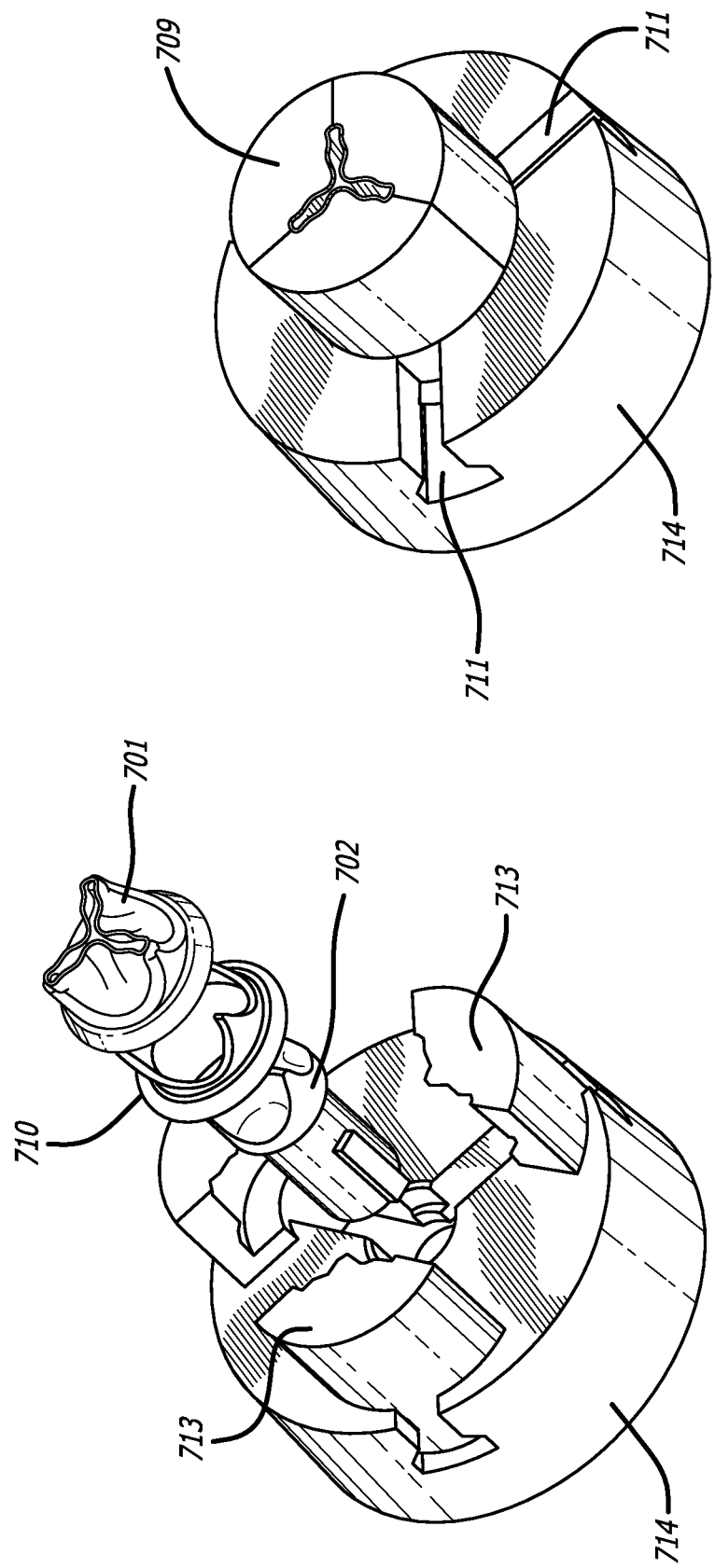
FIGS. 13A and 13B show an one example of an exploded view of a heart valve and stent on a mold and inserted into a mandrel for pressing a counter-mold against the heart valve on the mold.

Once the spraying step is complete, at the next step 905, as shown in FIG. 13A, the 3D mold 702 including the coating forming the heart valve 701, and the stent 710 in certain embodiments, is removed from the chuck 131 of the robot 132 and is inserted in a mandrel 714 including the counter mold 709. The mandrel 714 will accept the mold 702 in a recess.

Once inserted into the mandrel 714, at step 906, jaws 713 of the counter mold 709 are moved from the edge of the mandrel 714 towards the 3D mold 702 via the slots 711 of the mandrel 714 and pressed against the newly created valve on the 3D mold 702. The jaws 713 of the counter mold 709 can be moved towards the 3D mold 702 via the slots 711 manually or automatically. The design of the counter mold 709 can help to obtain a better surface quality and reduced porosity of the 3D heart valve 701. Additionally, as mentioned above, in some embodiments, hot pressing can be used to achieve an optimum finishing of the shape of the 3D heart valve 701, in such a way that such shape is closest to the 3D mold 702. Hot pressing also improves the mechanical features of the 3D valve 701.

Next, at step 907, the biocompatible fluid substance on the 3D mold 702 is cured. In one embodiment, the 3D mold may be cured in an oven between 70° and 90° Celsius for approximately 20 to 40 minutes. It is known that the temperature and time for curing in an oven could vary depending on the type of biocompatible fluid substance being used to form the 3D mold 702. The newly created heart valve 701 can be allowed to cool in situ. In another embodiment, the 3D mold may be cured without using an oven, for example, by cold curing the 3D mold with chemicals or other process.

After the spraying and curing processes, a portion of the mold the may extend past the ends (top side) of the jaws 713 of the counter mold 709. Before or after the curing process, preferably after the curing process, the portion of the mold extending past the jaws 713 is cut in order to form and obtain the desired shape of the valve leaflets. This cut of the mold affects the end portion (distal end) of the valve leaflets. In one embodiment, the cut to form the distal end of the leaflets is made with a blade, such as a scalpel. Also, the cut may be made with a robotic arm or machine using a blade, and in certain embodiments, the cut may be made manually. It has also been contemplated that a laser may be used to cut the distal end of the leaflets. The laser may be manually controlled or controlled by a machine or robotic arm.

Once the curing is complete, at step 908, the dry biocompatible fluid substance layer coated 3D mold 702, and stent in certain embodiments, on the support body 20 is extracted from the counter mold 709. The dry biocompatible fluid substance layer on the 3D mold 702 becomes final biocompatible 3D heart valve 701. Next, at step 909, the newly created 3D heart valve 701 is sterilized. The newly created 3D heart valve 701 includes the dried biocompatible fluid substance layer, and stent in certain embodiments. The valve 701 may be sterilized by wet or steam sterilization, dry heat sterilization, ethylene oxide, sporicidal chemicals, glass plasma, irradiation (gamma rays), or the like.

Next, at step 910, a surgeon may implant the 3D heart valve 701, including the stent in certain embodiments, in the heart of the patient. The synthetic heart valve 701 produced using the method 900, is cost effective, biocompatible, rapidly manufactured, highly customizable, and durable.

In some embodiments, the heart valve 701 can be produced directly from the 3D model 708, via 3D printing, CNC machining, or other methods. However, while typical production process might take several days, the spraying technique, as described in FIG. 9, for a singular valve can be completed less than 30-40 minutes. In addition to the increased speed of production, valves produced by the 3D spraying technique have very high biocompatibility and strong structural resistance. Therefore, the production process 900, as disclosed herein, dramatically decreases costs and permits easy production of variable sizes and geometries, making it suitable for veterinary use. This makes the process 900 ideal to for the application that requires low implant cost and great dimensional to accommodate the greatly varying valves of different species of animal. However, a person skilled in the art can appreciate that a prosthetic 3D human heart valve can also be produced using the process 900. It should also be appreciated that any type of prosthetic heart valve, such as a single leaflet valve, bileaflet valve, tilting disc valve, cage and ball valve, bicuspid valve, a mechanical valve, or the like may be used.

The foregoing description of specific exemplary embodiments will so fully reveal the invention according to the conceptual point of view, so that others, by applying current knowledge, will be able to modify and/or adapt in various applications the specific exemplary embodiments without further research and without parting from the invention, and, accordingly, it is meant that such adaptations and modifications will have to be considered as equivalent to the specific embodiments. The means and the materials to realize the different functions described herein could have a different nature without, for this reason, departing from the field of the invention, it is to be understood that the phraseology or terminology that is employed herein is for the purpose of description and not of limitation.

What is claimed:

1. A system for making a biocompatible three-dimensional heart valve, the system comprising:
    at least one delivery unit configured to deliver at least one biocompatible fluid substance towards a mold having a mold surface to obtain a coating layer of predetermined thickness configured for coating the mold surface, the biocompatible fluid substance having a plurality of particles;
    a handling unit configured to provide a relative movement with at least three degrees of freedom between the mold and the delivery unit, wherein the mold is coated with the at least one biocompatible fluid substance that is delivered to obtain a three-dimensional heart valve having a surface corresponding to the mold surface;
    a single suction and blowing device configured to generate a suction or blowing current, wherein the suction or blowing current removes from the mold any surplus particles of the biocompatible fluid substance supplied by the delivery unit; and
    a counter-mold that is adapted to press the coating layer deposited on the mold.

2. The system of claim 1, wherein the handling unit includes an anthropomorphic robot having a chain of pivot joints, the chain of pivot joints having a first end connected to a fixed base and a second end connected to a support base to which the mold is mounted in a removable way, the chain of pivot joints arranged to move the mold, according to at least 6 degrees of freedom.

3. The system of claim 1, wherein the handling unit includes a plurality of linear actuators, each actuator of the plurality having a first end engaged with a fixed base and a second end engaged with a support base to which the mold is mounted in a removable way.

4. The system of claim 1, wherein the suction and blowing device is fixed.

5. The system of claim 1, wherein the suction and blowing device is movable and associated with a motor arranged to move the suction and blowing device, the motor being configured to allow the suction and blowing device to follow spatially the position of the mold during its handling by the handling unit.

6. The system of claim 1, wherein the suction and blowing device includes a suction hood integral to the support base and configured to surround laterally the mold to maximize the suction of the surplus particles of the biocompatible fluid substance, and a suction tube arranged to connect pneumatically the suction hood with a suction system to generate a suction flow.

7. The system of claim 1, wherein the at least one delivery unit includes a first delivery unit arranged to deliver a first jet of a first biocompatible fluid substance towards the mold, the first biocompatible fluid substance being a biomaterial of synthetic origin, and a second delivery unit arranged to deliver a second jet of a second biocompatible fluid substance towards the mold, the second biocompatible fluid substance being a non-solvent, the second delivery unit arranged to direct the second delivery jet towards the mold in such a way that the second delivery jet is overlapped to the first delivery jet, inducing a quick deposit of the synthetic biomaterial supplied onto the mold from the first delivery unit obtaining a filamentous three-dimensional structure.

8. The system of claim 7, wherein the second biocompatible fluid substance is water.

9. The system of claim 7, wherein the at least one delivery unit further includes a plurality of delivery units arranged to deliver a plurality of biocompatible fluid substances.

10. The system of claim 9, wherein the plurality of biocompatible fluid substance includes a biopolymeric material of synthetic origin.

11. The system of claim 1, where the mold is three-dimensional.

12. The system of claim 2, further comprising at least one air compressor and at least one chemical container in communication with the delivery unit.

13. The system of claim 12, further comprising one or more continuous pumps attached to the fixed base, wherein the one or more continuous pumps deliver fluids from the chemical container to the delivery unit.

14. The system of claim 13, further comprising an electronic control unit in communication with the anthropomorphic robot, the electronic control unit supplies power and operating instructions to the anthropomorphic robot, continuous pumps, air compressor and the delivery unit.

* * * * *